United States Patent [19]
Lindquist et al.

[11] Patent Number: 6,063,358
[45] Date of Patent: May 16, 2000

[54] HIGH SURFACE AREA ALUMINA AND OTHER ALUMINUM PRODUCTS METHOD OF PREPARING BY SCHIFF BASE MEDIATED HYDROLYSIS PRODUCTS MADE THEREOF

[75] Inventors: David A. Lindquist, Benton, Ark.; Sterling S. Rooke, S. Burlington, Vt.

[73] Assignee: Board of Trustees of the University of Arkansas, Little Rock, Ark.

[21] Appl. No.: 09/054,910

[22] Filed: Apr. 3, 1998

Related U.S. Application Data

[60] Provisional application No. 60/043,045, Apr. 4, 1997.

[51] Int. Cl.$^7$ ............................ C01F 7/02; B01J 20/00; B01J 21/04
[52] U.S. Cl. ..................... 423/625; 423/628; 423/630; 502/414; 502/415; 502/439; 502/506
[58] Field of Search ..................... 423/625, 628, 423/630; 502/414, 415, 400, 506, 439

[56] References Cited

U.S. PATENT DOCUMENTS

| | | | |
|---|---|---|---|
| 3,950,478 | 4/1976 | Kenworthy et al. | 264/234 |
| 4,508,841 | 4/1985 | Onuma et al. | 502/73 |
| 5,412,128 | 5/1995 | Imuta et al. | 556/11 |
| 5,420,089 | 5/1995 | Tomotsu et al. | 502/103 |
| 5,457,173 | 10/1995 | Jensen | 528/9 |
| 5,561,093 | 10/1996 | Fujita et al. | 502/117 |

*Primary Examiner*—Tom Dunn
*Assistant Examiner*—Cam N. Nguyen
*Attorney, Agent, or Firm*—Gilbreth & Associates, P.C.; J. M. (Mark) Gilbreth

[57] ABSTRACT

A process for producing alumina and other aluminia products where the formation of a Schiff base imine by reaction of a orgaonaluminum amide or imide oligomer with a carbonyl compound is promoted by the Lewis acid character of the oligomer. The water byproduct of the Schiff base serves as an in situ reagent for subsequent hydrolysis and sol-gel condensation of the aluminum species with concomitant production of alkane. The imine then is washed from the alumina with a suitable solvent. Any of a number of primary amines and aldehydes or ketones may be reagents. Calcining of the sol-gels yields high surface area alumina as characterized by scanning electron microscopy, and gas physisorption measurements. Microporous and/or mesoporous alumina is obtained depending on synthesis conditions. Alumina microspheres are obtained under certain conditions.

20 Claims, 2 Drawing Sheets

HIGH SURFACE AREA ALUMINA AND OTHER ALUMINUM PRODUCTS METHOD OF PREPARING BY SCHIFF BASE MEDIATED HYDROLYSIS PRODUCTS MADE THEREOF

RELATED APPLICATION DATA

This application claims priority of U.S. provisional application 60/043,045 filed Apr. 4, 1997.

BACKGROUND OF THE INVENTION

1. Field of the Invention

The present invention relates to alumina, aluminum chelates and aluminoxanes, to methods of their making, and to products made thereof. In another aspect, the present invention relates to high surface area alumina, methods of making high surface area alumina, and to products made from high surface area alumina. In even another aspect, the present invention relates to methods of making high surface area alumina by Schiff base mediated hydrolysis. In still another aspect, the present invention relates to mesoporous alumina, to methods of making mesoporous alumina by Schiff base mediated hydrolysis, and to products made thereof. In yet another aspect, the present invention relates to a continuous process for making high surface area alumina. In even still another aspect, the present invention relates to a continuous process for making high surface area alumina by Schiff base mediated hydrolysis. In even yet another aspect, the present invention relates to a continuous process for making high surface area alumina by Schiff base mediated hydrolysis where the Schiff base product could be hydrolyzed to regenerate and allow recycle of the carbonyl compound and amine starting reagents. In still even another aspect, the present invention relates to varying the pore size of alumina. In still yet another aspect, the present invention relates to varying the pore size distribution of alumina. In yet even another aspect, the present invention relates to varying the mode of the pore distribution.

2. Description of the Related Art

Transition aluminas or activated aluminas are characterized by high specific surface areas making them useful for such applications as selective adsorbants, desiccants, and catalyst supports. The microstructure of alumina is strongly dependant upon synthesis conditions.

One of the problems related to the use of alumina as a catalyst support is deactivation by coke formation and pore plugging which hinders the diffusion of the reactants and products in and out of the catalyst particles. Large contribution of micropores to the specific surface area and wide pore size distribution both increase the deactivation rate. Conversely, high surface area aluminas with narrow pore size distributions that do not contain micropores lessen the deactivation rate. Therefore, synthesis of alumina with the proper pores size to reduce the deactivation rate that do not contain mircopores is of industrial interest.

The most common route to synthesize activated aluminas is via dehydration calcining of inorganic aluminum hydroxide gels obtained from the Bayer process. Aluminas may also be prepared by the hydrolysis and condensation of aluminum alkoxides. High surface area mesoporous alumina may additionally be obtained from an aluminum alkoxide with the aid of organic micelles.

The following are a sampling of the prior art related to making alumina.

U.S. Pat. No. 4,387,085 to Fanelli et al. discloses a process for preparing a high surface area alumina by heating a solution of alumina trialkoxide in a secondary or tertiary alcohol solvent to a sub-critical temperature at which the solvent decomposes to form water, and the water so formed hydrolyzes the aluminum trialkoxide. Solutions include aluminum tri-s-butoxide in s-butanol. The resultant aluminas have surface areas 500 $m^2/g$ or greater.

U.S. Pat. No. 4,617,183 to Lewis et al. discloses a process for the vapor phase production of alumina by introducing steam into the vapor space above a heated, liquid phase aluminum alkoxide in which the aluminum alkoxide is hydrolyzed in a heated reaction zone down stream from the liquid alkoxide and collected as a dry powder without the necessity for utilizing conventional drying processes.

U.S. Pat. No. 4,744,974 to Lewis et al. discloses a process for producing alumina wherein an aluminum trialkyl is reacted with a substantially water immiscible alcohol to produce an aluminum alkoxide and an alkane, the reaction between the aluminum trialkyl and the alcohol being conducted in an organic phase, the alkoxide being hydrolyzed in an aqueous phase which is in contact with the organic phase, the alumina formed by hydrolysis of the aluminum alkoxide being recovered from the aqueous phase.

U.S. Pat. No. 5,055,019 to Meyer et al. discloses a process for the preparation of boehmitic alumina compounds having a purity of at least 99.95% $Al_2O_3$. The compounds produced have a pore radii in the range of 3 to 100 nm. The preparation of such compounds is carried out by obtaining an alumina suspension from a neutral aluminum alkoxide hydrolysis, then aging the alumina suspension in an autoclave, preferably at a steam pressure of 1 to 30 barr which corresponds to at temperature of 100° C. to 235° C. for between 0.5 and 20 hours. The aging step of Meyer is preferably carried out with stirring at a peripheral speed of 1 to 6 m/s.

Fewer studies have been made using aluminum alkyl precursors. This is due to the extreme hydrolytic sensitivity of aluminum-carbon bonds. An example of a transition alumina prepared from aluminum alkyls is Catapal® produced by Vista Chemical Company. Catapal® is manufactured by the controlled oxidation of aluminum alkyls and hydrolysis of the resulting alkoxide in organic solvents using controlled amounts of water (Ziegler process). Catapal has high purity since refined aluminum metal is used as the aluminum source.

However, in spite of the prior art methods for producing alumina, they still suffer from one or more deficiencies as discussed above.

Thus there is a need in the art for new methods of making transition aluminas or activated aluminas.

There is another need in the art for making high surface are aluminas.

There is even another need in the art for making high surface area mesoporous alumina.

SUMMARY OF THE INVENTION

It is an object of this invention to provide for alumina, for a method for producing alumina, and for products made thereof.

It is another object of this invention to provide for high surface area alumina, for a method for producing high surface area alumina, and for products made thereof.

It is even another object of this invention to provide a method for high surface area mesoporous alumina, for a method of producing high surface area mesoporous alumina, and for products made thereof.

It is still another object of this invention to provide a method for the continuous production of alumina.

These and other objects of the present invention will become apparent to those of skill in the art upon review of this specification, including its drawings and claims.

According to one embodiment of the present invention there is provided a method of synthesizing high surface area alumina by Schiff base mediated hydrolysis. Generally, the method includes reacting an organoaluminum compound with a primary amine to form an organoaluminum derivative. The organoaluminum derivative is reacted with a carbonyl compound to form a Schiff base imine and aluminoxane. The aluminoxane is reacted with a primary amine and a carbonyl compound to form alumina and a second portion of imine.

According to another embodiment of this invention there is provided a method for preparing alumina or alumina composite. The method generally includes reacting an organoaluminum compound with a reactant to form an organoaluminum derivative. The organoaluminum derivative is reacted with a primary amine and a carbonyl compound to form an alumina composite and an imine.

According to even another embodiment of the present invention there is provided a method for preparing alumina. Generally the method includes reacting an organoaluminum compound with a primary amine to form an organoaluminum derivative. The derivative is reacted with a carbonyl compound to form a imine and aluminoxane. The aluminoxane is reacted with water to form alumina.

According to still another embodiment of the present invention there is provided a method for preparing aluminoxanes. Generally, the method includes reacting an organoaluminum compound with a primary amine to form an organoaluminum derivative. The derivative is reacted with a carbonyl compound to form an imine and aluminoxane.

According to yet another embodiment of the present invention there is provided a method for the continuous preparation of alumina. Generally, the method includes reacting an organoaluminum compound with a primary amine to form an organoaluminum derivative. The a first portion of the derivative is reacted with a carbonyl compound to form an imine and aluminoxane which is reacted with water to form alumina. The imine is reacted with water to form the carbonyl compound and the primary amine.

According to even still another embodiment of the present invention there is provided a method for the continuous preparation of alumina. Generally, the method includes reacting an organoaluminum compound with a primary amine to form an organoaluminum derivative. The derivative is reacted with a first portion of carbonyl compound to form a first portion of imine and aluminoxane. The aluminoxane is reacted with a second portion of primary amine and a second portion of carbonyl compound to form a second portion of imine and alumina. The imine is reacted with water to form a carbonyl compound and primary amine.

According to even yet another embodiment of the present invention there is provided a method for the continuous preparation of alumina. Generally, the method includes reacting an organoaluminum compound with a primary amine to form an organoaluminum derivative. The derivative is reacted with a carbonyl compound and a chelating imine to form a first aluminoxane chelate. The first aluminoxane chelate is reacted with an organoaluminum compound to form a second aluminoxane chelate. The second aluminoxane chelate is reacted with water to form an imine and alumina. The imine is reacted with the organoaluminum derivative of step.

According to still even another embodiment of the present invention there is provided a method for preparing alumina having a bimodal pore size distribution. Generally, the method includes reacting an organoaluminum compound with a primary amine to form an organoaluminum derivative. A first portion of the derivative is reacted with a first carbonyl compound of suitable molecular weight to produce a first portion of imine and a first portion of aluminoxane. The first portion of aluminoxane is reacted with water to produce alumina with a first mode with an average pore size distribution of $D_1$. A second portion of the derivative is reacted with a second carbonyl compound of suitable molecular weight to produce s second portion of imine and a second portion of aluminoxane. The second portion of aluminoxane is reacted with water to produce alumina with a second mode with an average pore size distribution of $D_2$.

According to still yet another embodiment of the present invention there is provided a method for preparing mixtures of alumina and aluminoxanes. Generally, the method includes reacting an organoaluminum compound with a primary amine to form an organoaluminum derivative. A first portion of the derivative is reacted with a carbonyl compound to form a first portion of aluminoxane and a first portion of imine. The first portion of aluminoxane is reacted with water to form alumina; A second portion of the derivative is reacted with a second portion of carbonyl compound to form a second portion of aluminoxane and a second portion of imine. The alumina prepared from the first portion of aluminoxane is combined with the second portion of aluminoxane to create a mixture.

These and other embodiments of the present invention will become apparent to those of skill in the art upon review of this specification, including its drawings and claims.

DETAILED DESCRIPTION OF THE INVENTION

Process Overview

Figure 1:
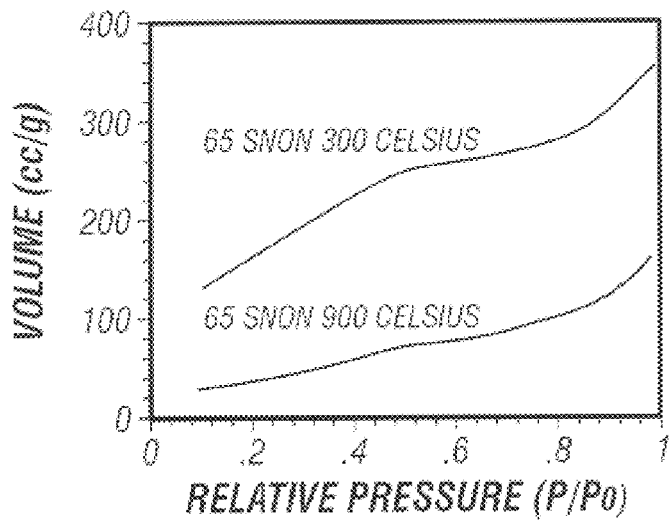
FIG. 1 is a graph showing the N2 Desorption isotherms for 65°Snon calcined to 300 C and 900° C.

The process of the present invention produces high surface area alumina by Schiff base mediated hydrolysis. The present invention involves the controlled in situ formation of a hydroxyl species or water followed by hydrolysis of the sensitive aluminum-carbon bond to yield an alumina precursor gel.

In the present invention, a Schiff base imine is formed by reaction of a organoaluminum amide or imide oligomer with a compound having an aldehyde or ketone functionality. The formation of the imine is promoted by the Lewis acid character of the oligomer. The hydroxyl species or water byproduct of the Schiff base serves as an in situ reagent for subsequent hydrolysis and sol-gel condensation of the aluminum species with concomitant production of an alkane. The imine then is washed from the alumina with a suitable solvent. Calcining of the sol-gels yields high surface area alumina as characterized by scanning electron microscopy, and gas physisorption measurements. Microporous and/or mesoporous alumina is obtained depending on synthesis conditions. Alumina microspheres are obtained under certain conditions. In addition, reducing the ratio of carbonyl containing reactants to organoaluminum derivative below the stoichiometric equivalent yields aluminoxanes.

Trialkyl aluminum compounds, however, are not ideal reagents for this method. Undesirable side products are obtained by the direct reaction of aluminum alkyls with aldehydes or ketones. Alternatively, if a heteroatom substituted aluminum alkyl is used, reaction of it with the carbonyl compound is inhibited. Heteroatom substitution reduces the electrophilicity of the aluminum so that the carbonyl compound may react to form the Schiff base rather than react directly with the aluminum alkyl. Therefore in the practice of the present invention, an organoaluminum amide or imide derivative or other heteroatom derivative is first prepared.

Formation of the Derivative

In the present invention, an organoaluminum amide or imide derivative is prepared. Preferably the organoaluminum derivative is prepared from a trialkyl aluminum compound $[R_3Al]$, a dialkyl aluminum compound $[R_2AlX]$, or an alkyl aluminum compound $[RAlX_2]$ where each R is independently an alkyl, X is hydrogen, a halogen or an alkene, more preferably, the organoaluminum derivative is prepared from triethyl aluminum, diethyl aluminum hydride or mixtures and combinations thereof. The derivative is preferably selected so that (1) the electrophilicity of aluminum is diminished; and (2) the derivative compound will provide an amide source for the Schiff base reaction.

The organoaluminum compound utilized in the present invention, comprises R groups, each of which is independently an alkyl group having in the range of 1 to 20 carbon atoms, preferably in the range of about 1 to about 6 carbon atoms, and more preferably in the range of about 1 to about 4 carbon atoms. The organoaluminum derivative may be prepared by contacting the organoaluminum with at least one reactant selected from the group consisting of ammonia, a primary amine, a hydrazine, substituted hydrazine, an hydroxyl amine, a primary amide or a combination or mixture thereof. Non-limiting examples of suitable primary amines include butyl amine, cyclohexylamine, aniline, phenylene diamine, 1, 6-hexanediamine or a combination or mixture thereof.

The reaction of the organoaluminum compound with the selected reactant to form the organoaluminum derivative, will generally take place under any conditions suitable to form the organoaluminum amide or imide derivative.

Generally, the organoaluminum compound and the selected reactant are contacted together at a temperature at which the reactants are in the gaseous or liquid phase, but below that temperature at which an aluminum nitride is formed. Such temperature is preferably at a temperature in the range of about −100° C. to about 500° C., more preferably at a temperature in the range of about 0° C. to about 200° C., and most preferably at a temperature in the range of about 25° C. to about 100° C.

Generally, the organoaluminum compound and the selected reactant are contacted together at a pressure to maintain the reactants in gaseous or liquid form at the reaction temperature. The pressure is preferably in the range of about 0.1 to about 10 atm., more preferably at a pressure in the range of about 0.1 atm. to about 2 atm., and most preferably at a pressure in the range of about 0.5 atm. to about 1.5 atm.

Generally, the organoaluminum compound and the selected reactant are contacted together for a period of time suitable to form the imide or amide derivative. Generally this reaction time is in the range of about 0.1 seconds to about 48 hours, preferably in the range of about 1 minute to about 2 hours, and more preferably in the range of about 5 minutes to about 1 hour.

In the preparation of the organoaluminum derivative, the organoaluminum and the reactant are contacted together at any ratio of organoaluminum:reactant that will produce the desired imide or amide derivative, for example, generally in the range of about 1:100 to about 10:1. However, it is preferred that at least a stoichiometric amount of reactant be provided for the organoaluminum. Therefore, the ratio of organoaluminum:reactant will preferably be in the range of about 1:100 to about 1:1, and more preferably be in the range of about 1:20 to about 1:1, and most preferably be in the range of about 1:5 to about 1:1.

In the preparation of the organoaluminum derivative the reaction may occur in a suitable solvent or without a solvent. Non-limiting examples of suitable solvents include: alkanes, such as hexane; aromatic solvents, such as benzene, toluene or xylene; ethers; tetrahydrofuran; or 1,2-dimethoxyethane.

While in the preparation of the organoaluminum derivative the reaction may be carried out in any suitable medium, it is preferably carried out under a nitrogen or other inert atmosphere.

In the practice of the present invention, the organoaluminum compound or the organoaluminum derivative described above may be further contacted with other compounds known to form bonds with organo aluminum. Non-limiting examples of such compounds include: aluminum alkoxide; aluminum halide; alumina chelate; organophosphate ester; and a silicon compound containing a nitrogen or oxygen atom bonded to the silicon. As a non-limiting example, alumina phosphate can be prepared using an alkyl phosphate derivative of diethyl aluminum. These compounds may be introduced at any time in the practice of the present invention.

Schiff Base Reaction

The organoaluminum derivative is reacted with at least one carbonyl compound having an aldehyde [HRC=O] or ketone [$R_2$C=O] functionality to form either an aluminum Schiff base complex, a mixture of Schiff base and aluminoxane or a mixture of Schiff base and alumina precursor gel. The compound having an aldehyde [HRC=O] or ketone [$R_2$C=O] functionality may be used individually or in mixtures or combinations of different carbonyl compounds.

Optionally, additional quantities of ammonia, primary amine, hydrazine, substituted hydrazine, or a combination or mixture thereof may be added to form the aluminum Schiff base complex or a mixture of Schiff base and alumina precursor gel.

The Schiff base condensation reaction may occur with or without the presence of solvents. Non-limiting examples of suitable solvents include the following: alkanes, such as hexane; aromatic solvents, such as benzene, toluene, or xylene; ethers, such as tetrahydrofuran, or 1,2-dimethoxyethane.

The reaction of the organoaluminum derivative and the compound or compounds having carbonyl functionality, will generally take place under any conditions suitable to form the aluminum Schiff base complex, a mixture of Schiff base and aluminoxane or a mixture of Schiff base and alumina precursor gel.

Generally, reaction between the organoaluminum derivative and the compound or compounds having carbonyl functionality is exothermic. Thus, the reaction is cooled to the extent necessary to maintain the reaction in the range at which the reactants are in the gaseous or liquid phase and at a temperature necessary to avoid unwanted side reactions. The reaction temperature is generally in the range of about −100° C. to about 300° C., preferably in the range of about −78° C. to about 100° C., and more preferably in the range of about 0° C. to about 80° C.

Generally, the organoaluminum derivative and the functional compound are contacted together at a pressure to maintain the reactants in gaseous or liquid form at the reaction temperature, preferably in the range of about 0.1 to about 10 atm, more preferably at a pressure in the range of about 0.1 atm to about 2 atm, and most preferably at a pressure in the range of about 0.5 atm to about 1.5 atm.

Generally, the organoaluminum derivative and the functional compound are contacted together for a period of time suitable to produce the desired imine. Generally the reaction time is in the range of about 0.1 seconds to about 48 hours, preferably for a period of time in the range of about 1 minute to about 2 hours, and more preferably for a period of time in the range of about 3 minutes to about 30 minutes.

In the preparation of the aluminum Schiff base complex, a mixture of Schiff base and aluminoxane or a mixture of Schiff base and alumina precursor gel, the organolaluminum derivative and the Schiff base precursors are contacted together at any suitable ratio that will produce the desired Schiff base and the desired aluminum complex, aluminoxane or alumina precursor.

The use of larger molecular weight amines or carbonyl compounds result in alumina with relatively larger pore size as compared to the aluminas which result from the use of smaller molecular weight amines or carbonyl compounds. Thus, the pore size may be varied by the practice of the present invention. Also, monomodal or polymodal pore size distribution may be tailored by the selection of the amines and/or carbonyl compounds. A mode is distributed around an average pore diameter and will comprise a threshold percentage of total pore volume. It is understood, for example, that alumina having a bimodal pore size distribution may be produced if reactants, selected to create a pore size distribution of average $D_1$ and a pore size distribution average of $D_2$, are both utilized. The resulting alumina would then comprise a first mode with an average pore size distribution of $D_1$ and a second mode with an average pore size distribution of $D_2$ with the relative amount of alumina in each mode dependent upon the amount of reactants selected. This can obviously be carried out for any number of modes to form a polymodal distribution of mode N.

In addition, aluminoxanes may be prepared by the above method by varying the amount of carbonyl compound. If, for example, the ratio of organoaluminum derivative:carbonyl is about 1:1, then an average of one aluminum-carbon bond remains on each aluminum atom and an aluminoxane, as opposed to the alumina precursor, is formed.

Moreover, the aluminoxane thus formed may be converted to an alumina precursor by direct addition of water or by water produced by Schiff base condensation. In the case of an aluminoxane with an average of one aluminum-carbon bond per aluminum atom, one water molecule per aluminum atom is required to prepare an alumina precursor.

Furthermore, aluminum chelates may be prepared by the above method if the imine has additional chelating functionality. In that case, the imine chelate would bond to the aluminum.

In situ water or an hydroxyl species is produced as the by product of a Schiff base condensation of any primary amine with any of a number of compounds having carbonyl functionality. For illustrative purposes, reaction (1) shows how in situ water is produced as the by product of a Schiff base condensation of ammonia with acetone.

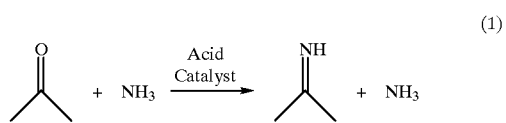

Reaction (1) is catalyzed by an aluminum derivative in the solution. In principle, the Schiff base and hydroxyl species or water can be formed by the reaction of any organoaluminum amide or imide derivative or primary amine with any of a number of carbonyl compounds in the presence of an optional acid or base catalyst.

As a non-limiting example, the electrophilicity of a triethylaluminum $[(CH_3CH_2)_3Al]$ is tempered by reaction with a ammonia to form the cyclic aluminum alkyl amide $[CH_3CH_2)_2AlNH_2]_x$ (where x=2 or 3) with the evolution of ethane. Assuming for simplicity that the aluminum alkyl amide is a dimer, the stoichiometry of the reaction series using acetone is represented by reaction (2).

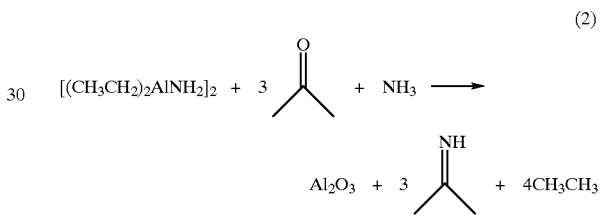

A proposed mechanism for the initial reaction of aluminum amide derivative with a compound with carbonyl functionality of reaction (2) is shown below in reaction scheme 1.

Reaction Scheme 1:
Proposed initial reaction of aluminum amide derivative with carbonyl carbon.

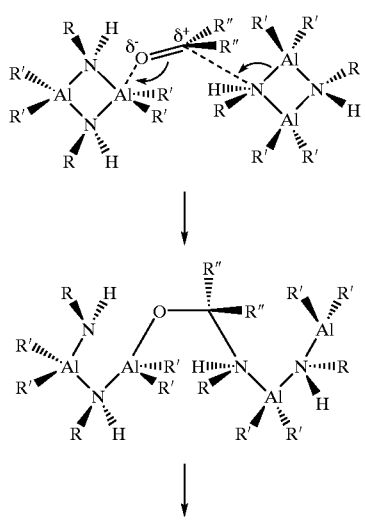

-continued

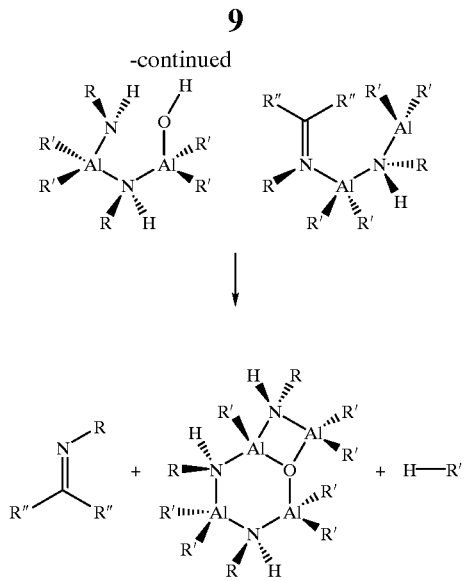

Reaction Scheme 1: Proposed initial reaction of aluminum amide derivative with carbonyl carbon.

Based on steric considerations it is reasonable to assume that two amide molecules participate in ketone activation according to Reaction Scheme 1. Subsequent similar reactions with additional acetone serve to add oxygen and remove nitrogen from the developing aluminoxane or alumina precipitate with concomitant production of ethane and imine. The water byproduct normally produced by Schiff base condensation was instead incorporated into producing ethane and network aluminum oxygen bonds respectively. Moreover, since an amide rather than an amine was used as a Schiff base reagent, in actuality one equivalent of an hydroxyl (OH) rather than a water molecule were produced since an amide has one less hydrogen atom than an amine.

If the reaction series is continued until all of the amide functions are liberated to form imine than each aluminum atom still retains the equivalent of one ethyl group per aluminum. Therefore, an aluminoxane rather than an alumina precursor has been formed at this stage. Structure 1 below illustrates an idealized structure for the aluminoxane.

Structure1: Aluminoxane (RAIO) Structure

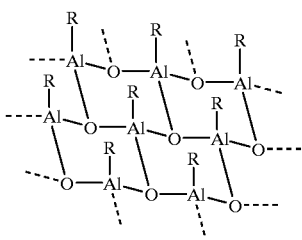

Structure 1: Aluminoxane (RAIO) Structure

Note from reaction (2), above, that the aluminum amide has insufficient nitrogen for complete reaction with the ketone or aldehyde and an additional equivalent of primary amine is needed. An additional equivalent of acetone and excess ammonia may be added to the aluminoxane. Since ammonia rather than an amide function is used in this second Schiff base reaction, an equivalent of a water molecule rather than a hydroxyl is produced. Finally, after washing the imine from the hydrolyzed precipitate and calcining, high surface area transition alumina is obtained.

Also the Schiff base product of reaction (2) is unstable, and condenses. For illustrative purposes reaction (3) shows that the isopropylideneimine Schiff base product of reaction (2) condenses to form the more stable 2,2,4,4,6-pentamethyltetrahydropyrimidine.

(3)

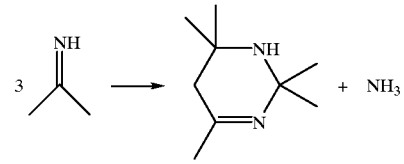

Polymeric, rather than molecular, imine condensates are formed when the synthesis is conducted in hot solution. The majority of imine (polymeric or molecular) can be washed from the alumina prior to calcining with a suitable solvent.

Formation of the precurser gel

The water produced as the by product of the Schiff base condensation reaction, as described above, then reacts to hydrolyze and cross-link the organoaluminum derivative to form an alumina precursor gel with the concomitant production of an alkane. This is illustrated in simplified form in reaction (4).

(4)

The precursor gel may be calcined as is well known in the art. Generally the calcining will be carried out at a temperature in the range of about 200° C. to about 900° C., for calcining times in the range of about 30 minutes to about 24 hours, although it should be understood that higher or lower calcining temperatures and times may be utilized.

Continuous Reaction

A Schiff base product in the present invention could be hydrolyzed to regenerate the carbonyl compound and amine starting reagents. This would allow for operation of a continuous alumina synthesis process utilizing hydrolysis of the imine byproduct to make fresh reagents. Alternatively, use of alkyl or aryl primary amines ($RNH_2$) reagents would yield monomeric imine Schiff bases amenable to reversible hydrolysis. Reaction Scheme 2 illustrates a proposed idealized process.

Reaction Scheme 2:
Proposed Continuous Process for Alumina Synthesis

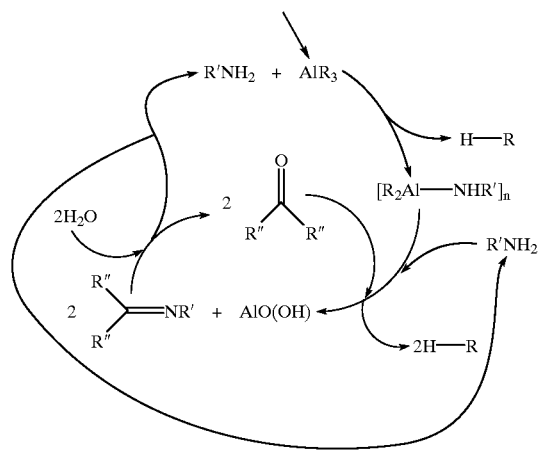

Reaction Scheme 2: Proposed Continuous Process for Alumina Synthesis

Reaction scheme 2 may be modified so that lesser quantities of primary amine and carbonyl compound may be utilized in a continuous process. For example, in one equivalent of the carbonyl compound and one equivalent of primary amine are used rather than two equivalents of each, an aluminoxane rather than alumina precursor is formed at the bottom of the cycle. The aluminoxane thus formed may be hydrolyzed to an alumina precursor by direct addition of water. The single equivalent of imine may thene be hydrolyzed to regenerate one equivalent each of the amine and carbonyl compound for the cycle.

The residual chemical potential energy of the imine towards hydrolysis is a major factor in such a continuous process. The success of Reaction Scheme 2 is dependent upon synthesizing the imine at moderate temperatures to minimize formation of condensates which may not be reversibly hydrolyzed.

The aluminas of the present invention find utility in a wide range of applications as are known for prior art aluminas. For example, the aluminas of the present invention find utility as desiccants and as catalyst supports.

The aluminoxanes of the present invention find utility in a wide range of applications as are known for prior art aluminoxanes. For example, as co-catalysts in polyolefin process. In addition, although aluminoxanes are generally used as co-catalyst in polyolefin process, mixtures of alumina and aluminoxanes synthesized according to the present invention may also be used as co-catalysts in polyolefin process. For example, fine alumina suspensions coated with aluminoxanes may function as co-catalysts.

Any of the intermediate products of the present invention find utility in the making of alumina and/or aluminoxanes of the present invention.

Many other Schiff base precursors other than ammonia and acetone may be utilized in the invention. For example, if benzaldehyde and ammonia are used as Schiff base precursors, then the benzylamine ($C_6H_5CH=NH$) product will be converted to hydrobenzamide [$(C_6H_5CH=NH)_2CH(C_6H_5)$] according to the equilibrium shown in reaction 5.

Reaction 5.
Hydrobenzamide formation eqilibrium

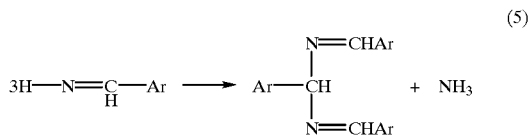

(5)

Reaction 5. Hydrobenzamide formation equilibrium

The hydrobenzamide formed in Reaction 4 may serve to inhibit subsequent direct hydrolysis by forming a chelate with the alumoxane as in Structure 2 below.

Structure 2 chelation of hydrobenzamide to intermediate alumoxane species

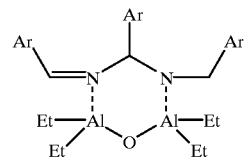

Structure 2 chelation of hydrobenzamide to intermediate alumoxane species

The stoichimetry is somewhat more complex than other systems since hydrobenzamide is formed from three equivalents of benzaldehyde. Reaction Scheme 3, below, illustrates a proposed first and second generation continuous boehmite synthesis using hydrobenzamide. The structures of hydrobenzamide and the two proposed alumina species intermediates are included in Reaction Scheme 3 for clarification.

Reaction Scheme 3.
Proposed method for boehimite synthesis using hydrobenzamide.

First Generation:

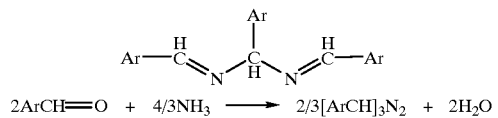

$2ArCH=O + 4/3NH_3 \longrightarrow 2/3[ArCH]_3N_2 + 2H_2O$

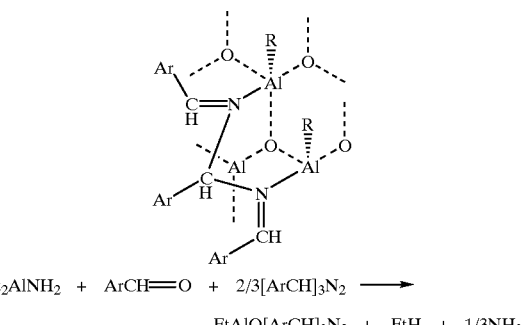

$Et_2AlNH_2 + ArCH=O + 2/3[ArCH]_3N_2 \longrightarrow$ $EtAlO[ArCH]_3N_2 + EtH + 1/3NH_3$ $Et_2AlO[ArCH]_3N_2 + Et_3Al \longrightarrow$

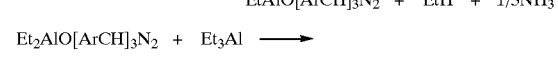

-continued

Et$_4$Al$_2$O[ArCH]$_3$N$_2$

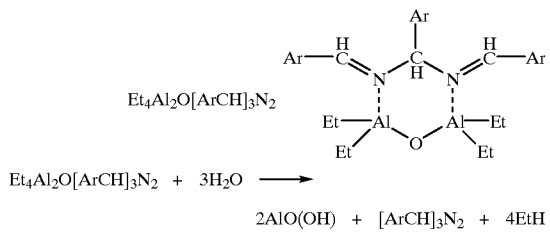

Et$_4$Al$_2$O[ArCH]$_3$N$_2$ + 3H$_2$O ⟶

2AlO(OH) + [ArCH]$_3$N$_2$ + 4EtH

Second Generation:

[ArCH]$_3$N$_2$ + 1.5Et$_2$AlNH$_2$ + 1.5ArCH=O ⟶

1.5EtAlO[ArCH]$_3$N$_2$ + 1.5EtH + 1/2NH$_3$ 1.5EtAlO[ArCH]$_3$N$_2$ + 1.5Et$_3$Al ⟶ 1.5Et$_4$Al$_2$O[ArCH]$_3$N$_2$ 1.5Et$_4$Al$_2$O[ArCH]$_3$N$_2$ + 4.5H$_2$O ⟶

3AlO(OH) + 1.5[ArCH]$_3$N$_2$ + 6EtH

In the first step of Reaction Scheme 3, imine (hydrobenzamide) may be prepared prior to addition of the alkyl alumina derivative. Also, trialkyl alumina may be added directly in the third step of the first generation in lieu of prior conversion to an alkyl aluminum derivative.

EXAMPLES

The following examples are provided merely to illustrate the present invention, and are not intended to limit the scope of the claims.

All syntheses were conducted under N$_2$ atmosphere under oil bubbler purge using Schlenk techniques. Hexane solvent was freshly distilled from sodium benzophenone ketyl. Dry acetone was obtained by distillation from anhydrous potassium carbonate. Triethyl aluminum (93%) was used as received (Aldrich Chemical Co.). Anhydrous ammonia from a lecture bottle was used (Matheson Gas Co.).

Sample Designations

The product microstructure is dependent on reaction conditions so each sample is code named according to three reaction variables. The variable of synthesis bath temperature is denoted by degrees Centigrade (−78°=−78° C.=acetone-dry ice, 0°=0° C.=water-ice, 65°=65° C.=heated oil bath). Under some conditions the product is formed both as precipitate and as a supernatant suspension in the same flask. These fractions from the same reaction vessel are designated by a letter "P" or "S" respectively. The "P" or "S" designation is not used if a reaction yielded only a precipitate without a supernatant fraction. Finally, the acronyms "sto" and "non" denote whether the material was prepared with a stoichiometric or excess of acetone reagent respectively. For example, alumina product from the supernatant fraction of a reaction run in a 65° C. oil bath, and using excess acetone is named "65°Snon".

Water-Ice Bath, Stoichiometric (0°sto) Synthesis

The diethyl aluminum amide [(CH$_3$CH$_2$)$_2$AlNH$_2$]$_x$ was prepared using the method of Interrante and coworkers. To a 250 mL flask equipped with a septum inlet, magnetic stir bar, and water condenser was syringed 40 mL of hexane and 8 mL (58.5 mmol) of triethylaluminum. The flask was heated to 60° C. in an oil bath and ammonia gas bubbled through the solution to form the amide. The reaction was complete when ethane gas evolution had ceased. Ammonia addition was then ceased and the solution cooled to 0° C. in a water/ice bath. After cooling, 6.44 mL (87.8 mmol) of acetone was slowly syringed into the flask with stirring. The acetone addition was accompanied by formation of a white slurry in the flask and vigorous ethane gas evolution as verified by gas phase infrared spectroscopy. When gas evolution had ceased, ammonia gas was again bubbled through the mixture initiating further gas production and precipitate formation. After several minutes ammonia addition was ceased and the reaction flask was allowed to stand overnight undisturbed under nitrogen purge. On the following day, the alumina precipitate was filtered from the mixture using a glass frit and washed liberally with hexane in air, yielding 3.432 g of product. Copious crystalline needles (4.03 g) of the monohydrate of the pyrimidine derivative (1) were obtained from the evaporated hexane washings (80.8% yield based on moles of acetone used). The melting point of the monohydrate of (1) was 42° C. (Literature value 43–44° C.).

Dry Ice-Acetone Bath, Stoichiometric (−78°sto) Synthesis

The procedure was the same as for 0°sto except that the flask was cooled in a dry ice/acetone bath during acetone addition and subsequent excess ammonia addition. The weight of hexane washed product was 3.202 g.

Oil Bath, Stoichiometric (65°sto) Synthesis

The procedure was the same as for 0°sto except that the flask was not cooled during acetone addition, but maintained at 65° C. throughout the synthesis. The weight of brown colored precipitate obtained after washing with hexane and air drying was 4.27 grams. Unlike 0°sto, the imine condensate was polymeric and not completely removed by washing, hence the coloration and greater mass of product as compared to 0°sto.

Hot, Nonstoichiometric (65°Snon) and (65°Pnon) Synthesis

The same general procedure was used. The quantities of reagents were 10 mL (73.1 mmol) of triethylaluminum and 10 mL (136 mmol) of acetone (24% excess). At the end of the reaction, ammonia addition was ceased after nearly all visible gas evolution from the solution had subsided. The flask then was allowed to cool overnight at room temperature under nitrogen purge. On the following day, a milky colloidal suspension had formed in the supernatant. The colloidal supernatant was decanted from the firm precipitate and filtered but, without washing with hexane as in the other syntheses. After air drying for a day the weight of the supernatant residue (65°Snon) was 1.39 g. The weight of the precipitate (65°Pnon), without washing with hexane, was 7.41 g.

Calcining Procedures

Samples of precursors from all syntheses were calcined in air in a muffle furnace at various temperatures ranging up to 900° C. Every sample was heated from raw product (washed or unwashed) to temperature and held at temperature for 3 hr. before cooling. The 900° C. heated sample of 0°sto was also subsequently heated in a steam atmosphere to verify its thermochemical stability. Steam treatment was accomplished using a tube furnace by exposing the sample to a stream of air from a water bubbler for 3 hours at 900° C.-

Characterization Methods

The imine crystals of (1) isolated from the low temperature preparations were recrystallized to obtain their $^1$H and $^{13}$C NMR spectra in $C_6D_6$ solution using a Bruker 200 MHz FT-NMR. Surface analyses of calcined alumina using $N_2$ isotherms including: 5 point BET specific surface areas (adsorption) ($0.05 \leq P/P_o \leq 0.35$), and 25 point Barrett-Joyner-Halenda (BJH) calculated pore size distributions (desorption) ($0.05 \leq P/P_o \leq 0.99$) were obtained with a NOVA-1200 instrument (Quantachrome Corp.). The average pore radius was calculated from twice the pore volume divided by the surface area. Samples were outgassed under vacuum at 250° C. prior to surface analyses. Scanning electron microscopy of calcined samples was accomplished using plasma gold coated samples in an ISI-DS-130 instrument.

C—H resonances: $\{[(CH_3)_2, \sigma\ 0.90]; [CH_2, \sigma\ 1.34]; [(CH_3)_2, \sigma\ 1.44]; [CH_3, \sigma\ 1.79]\}$, and a small broad N—H peak at 5.16 ppm. The $^{13}$C NMR spectrum has nine resonances since all carbons of the pyrimidine are inequivalent in solution. Eight of the $^{13}$C resonances lie between 70 and 15 ppm, the imine carbon peak occurs far downfield at 161 ppm.

Compound (1) is catalytically sensitive to moisture and decomposes to an orange then red liquid after several days of storage in a screw cap vial at room temperature. The color is likely due to formation of conjugated oligomers by aldol condensation in the presence of hydrogen ions from moisture. Aldol condensation of imines involves two species: a protonated imine and an enamine tautomer of the imine as shown below.

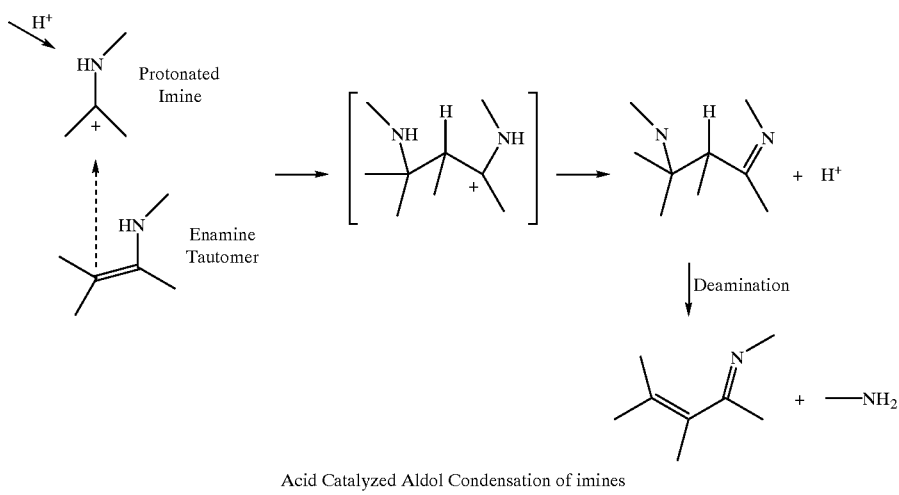

Acid Catalyzed Aldol Condensation of imines

Results and Discussion

1. Schiff Base Chemistry

It is accepted that the intermediate in forming a Schiff base involves an acid activated carbonyl attacked by a nucleophilic amine. For the system here, two diethylaluminumamide molecules may be involved in forming the intermediate, one molecule providing the acid catalyst and the other providing the attacking amine (amide) as shown below.

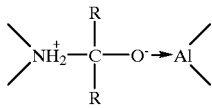

The isopropylidenimine product from the intermediate is not stable. Small molecule Schiff base imines formed from ammonia and alkyl substituted aldehydes and ketones condense to form more stable compounds. If the sol-gel synthesis is conducted at cold temperatures, then the supernatant solution contains the imine compound (1) formed from three isopropylidenimine molecules. The $^1$H NMR spectrum of the pyrimidine derivative in $C_6D_6$ shows four singlet The coloration in the alumina products from the syntheses run at 65° C. is also likely due to thermally induced condensation reactions similar to the decomposition of (1) as in Reaction Scheme 1.

2. Alumina Properties

The microstructure of the alumina is strongly dependent upon synthesis conditions. A microporous alumina is obtained from the synthesis conducted at 65° C. using excess acetone (24% excess). The excess organic in the material before firing may have inhibited formation of a mesoporous layered structure typical of transition aluminas. The 65°Pnon and 65°Snon samples from this reaction have high specific surface areas as shown in Tables 1 and 2.

TABLE 1

65° Pnon Surface Area and Weight Loss of Calcines

| Temperature | Total Wt. Loss | BET Area |
|---|---|---|
| 200° C. | 37.0% | 370 (m²/g) |
| 300° C. | 50.1% | 498 (m²/g) |
| 400° C. | 55.1% | 431 (m²/g) |
| 500° C. | 44.0% | 378 (m²/g) |

TABLE 2

65° Snon Surface Area and Weight Loss of Calcines

| Temperature | Total Wt. Loss | BET Area (m²/g) | Total Pore Volume |
|---|---|---|---|
| 200° C. | 42.0% | 470 | 0.44 cc/g |
| 300° C. | 39.5% | 621 | 0.55 cc/g |
| 400° C. | 58.9% | NA | NA |
| 500° C. | 72.1% | 618 | NA |
| 600° C. | NA | 575 | NA |
| 900° C. | NA | 208 | 0.255 cc/g |

The supernatant fraction has a somewhat higher surface area than the precipitate at each calcining temperature. The high weight losses for these materials is due to the fact that the imine condensates were not washed out of the products prior to calcining. The $N_2$ desorption isotherms for 65°Snon heated to 300° C. and 900° C. respectively are shown in FIG. 1. Both calcines have some microporosity and the change in slope at a relative pressure ($P/P_o$) of 0.47 in the 300° C. sample isotherm indicates some degree of mesoporosity present in this material.

The high surface areas of the 65°Snon calcines would make them potentially useful as adsorbents. The water adsorption capacity of the 500° C. calcined 65°Snon was 11.3 wt. % after 40 hours under 9% relative humidity and 43.6 wt. % after 15 hours at 100% relative humidity. These values are comparable to the capacities of commercial alumina desiccants.

Figure 2:
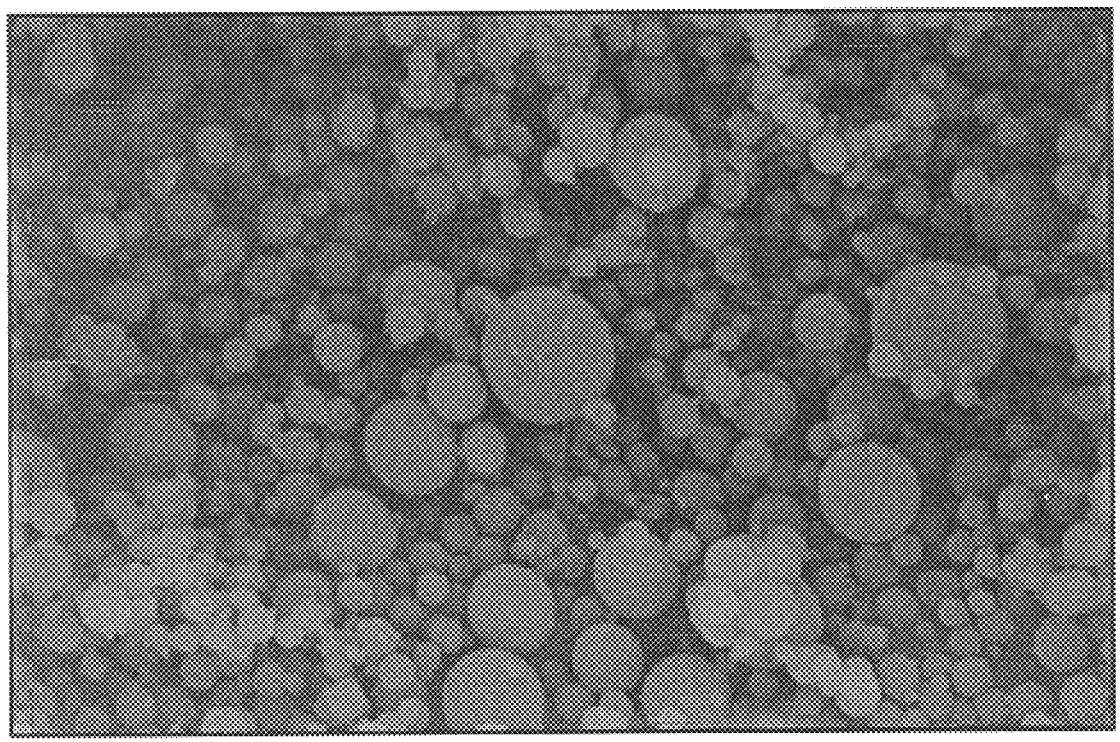
FIG. 2 is an SEM of 65°Snon calcined to 600° C.
Figure 3:
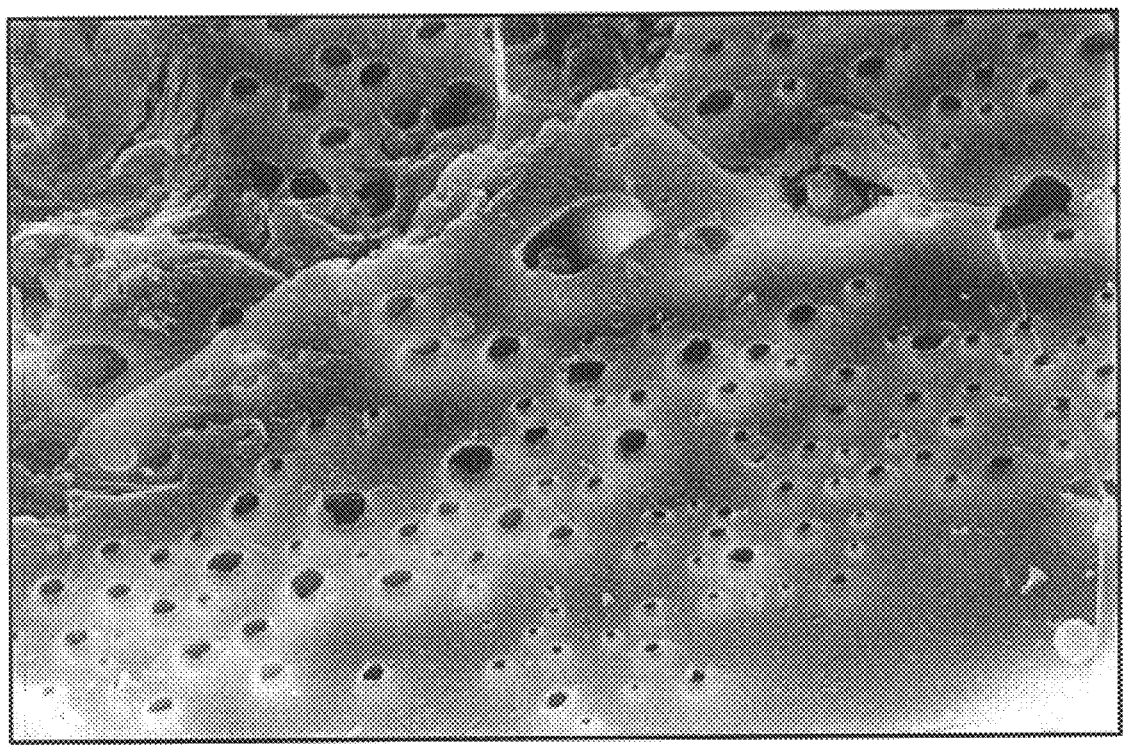
FIG. 3 is an SEM of 65°Pnon calcined to 300° C.

Scanning electron microscopy of the 65°Pnon and 65°Snon samples revealed striking differences. FIG. 3 is scanning electron micrograph of 65°Snon material after calcining to 600° C. in air. The morphologies of 65°Snon calcines heated at 300° C. and 900° C. are similar to that seen in FIG. 2. The 65°Pnon material is quite different as shown in FIG. 3.

The plastic morphology of 65°Pnon suggests that the initially pliable precipitate is incompletely reacted and undergoes further condensation with concomitant gas evolution leaving bubbles in the structure. By contrast, the microsphere fraction (65°Snon) forms in the dilute supernatant after the precipitate has formed. Microsphere growth from solutions has been investigated by a number of workers and it is generally accepted that growth is most uniform in dilute solutions. Interestingly, growth of microspheres proceeds by accretion of smaller sol particles rather than through primary growth of individual sol particles.

In contrast with the synthesis using excess acetone, the three syntheses using stoichiometric reagents have smaller surface areas at each calcining temperature and, with the exception of the synthesis using dry ice-acetone bath (−78°sto), are mesoporous. Surface analyses and weight loss data for calcines from the stoichiometric syntheses are compiled in Table 3.

TABLE 3

Weight Loss and Surface Analyses Data for Stoichiometric Syntheses

| Sample | Temperature | Total Wt. Loss | BET Area | Total Pore Volume | Ave. Pore Radius |
|---|---|---|---|---|---|
| 0° sto | 300° C. | 15.7% | 281 (m²/g) | 0.127 cc/g | 9.04Å |
|  | 600° C. | 32.2% | 211 (m²/g) | 0.192 cc/g | 18.2Å |
|  | 900° C. | 41.5% | 97.7 (m²/g) | .084 cc/g | 17.2Å |
|  | 900° C./steam | NA | 66 (m²/g) | 0.133 cc/g | 34.2Å |
| −78° sto | 650° C. | 28.2% | 292 (m²/g) | 0.180 cc/g | 12.3Å |
| 65° sto | 650° C. | 51.0% | 283 (m²/g) | 0.235 cc/g | 16.6Å |

Figure 4:
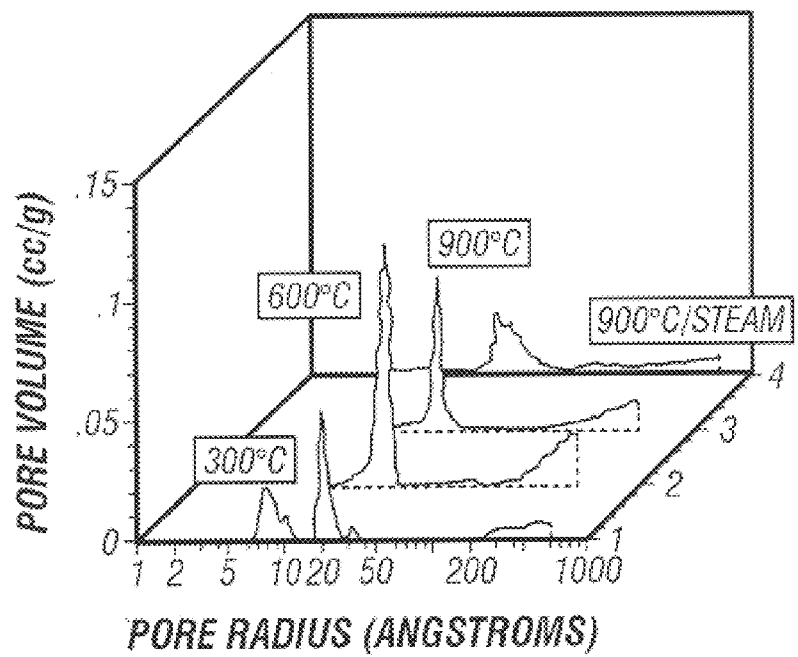
FIG. 4 is a graph of the BJH pore size distributions for 0° sto calcines.

FIG. 4 shows stacked pore size distributions of the calcined and steam/calcined 0°sto samples calculated using the BJH method from the $N_2$ desorption isotherms.

It is clearly evident from FIG. 4 that all of the 0°sto calcines contain mesopores with radii on the order of 20 Å. The 0°sto 300° C. calcine also has a significant fraction of micropores. The sample heated to 600° C. has the greatest degree of mesoporosity typical of transition aluminas activated at intermediate temperatures. The material retains a BET surface area of 66 m²/g after heating under the harsh conditions of a steam atmosphere at 900° C. The BJH pore size distribution of the 65°sto sample heated to 650° C. (not shown) is similar to the 0°sto heated similarly. However, the −78°sto sample has more microporosity (average pore radius 12.3Å) than either the 0°sto or 65°sto calcines. Apparently, the slower kinetics at −78° C. inhibits formation of a precursor which leads to the thermodynamically stable layered mesoporous phases typical of transition aluminas.

Conclusion

The synthesis of both microporous and mesoporous high surface area aluminas has been demonstrated using a method of in situ hydrolysis of triethylaluminum followed by calcining. Calcines having a degree of microporosity are formed when sol-gel synthesis is conducted at cold (dry ice) temperatures or when excess acetone is used. Conversely, a mesoporous material is obtained using stoichiometric quantities of acetone at moderate temperatures (0° C. or 65° C.). Based on energetics this process is a potential alternative to current preparative methods for high purity transition aluminas. Synthesis of the alumina precursor is rapid due to the high potential energy of the triethylaluminum reagent. Also, some residual energy remains in the imine Schiff base by product. Therefore, the method may be amenable to the development of a continuous process whereby the imine by product could be hydrolyzed to regenerate reagents for the synthesis. The continuous process may or may not require that one separate the regenerated amine and carbonyl compounds at the end of each synthesis cycle. Moreover, unhydrolized imine may be incorporated into the process during each synthesis cycle.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A method for preparing alumina comprising:
   (a) contacting an organo aluminum compound with a first reactant to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;
   (b) contacting a first carbonyl compound comprising an aldehyde or ketone with the organoaluminum derivative of step (a) to form a first portion of imine and aluminoxane; and
   (c) contacting the aluminoxane of step (b) with a second reactant and a second carbonyl compound comprising an aldehyde or ketone to form alumina and a second portion of imine;
   wherein the first reactant and second reactant are selected from the group consisting of: ammonia, primary amine, hydrazine, substituted hydrazine, hydroxyl amine and mixtures and combinations thereof.

2. The method of claim 1 further comprising:
   (d) calcining the alumina of step (c).

3. The method of claim 1 wherein the organo aluminum compound is selected from the group consisting of: a trialkyl aluminum, a dialkyl aluminum halide, a dialkyl aluminum hydride, an alkyl aluminum dihalide, an alkyl aluminum dihydride and mixtures and combinations thereof.

4. A method for preparing alumina or alumina composite comprising:
   (a) contacting an organoaluminum compound with a reactant to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes, and wherein the reactant is selected from a group consisting of aluminoxane, aluminum alkoxide, organophosphate ester, and silicon compound containing a nitrogen or oxygen atom bonded to the silicon;
   (b) contacting the organoaluminum derivative of step (a) with a primary amine and a carbonyl compound comprising an aldehyde or ketone to form an alumina composite and an imine.

5. A method for preparing alumina comprising:
   (a) contacting an organoaluminum compound with a reactant to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;
   (b) contacting a carbonyl compound comprising an aldehyde or ketone with the organoaluminum derivative of step (a) to form a imine and aluminoxane; and
   (c) contacting the aluminoxane of step (b) with water to form alumina;
   wherein the reactant is selected from the group consisting of: ammonia, primary amine, hydrazine, substituted hydrazine, hydroxyl amine and mixtures and combinations thereof.

6. The method of claim 5 further comprising:
   (d) calcining the alumina of step (c).

7. The method of claim 5 wherein the organoaluminum compound is selected from the group consisting of: a trialkyl aluminum, a dialkyl aluminum halide, a dialkyl aluminum hydride, an alkyl aluminum dihalide, an alkyl aluminum dihydride and mixtures and combinations thereof.

8. A method for preparing aluminoxanes comprising:
   (a) contacting an organoaluminum compound with a primary amine to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;
   (b) contacting a carbonyl compound comprising an aldehyde or ketone with the organoaluminum derivative of step (a) to form an imine and aluminoxane.

9. A method for the continuous preparation of alumina comprising:
   (a) contacting an organoaluminum compound with a primary amine to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;
   (b) contacting a carbonyl compound comprising an aldehyde or ketone with a first portion of the organoaluminum derivative of step (a) to form an imine and aluminoxane;
   (c) contacting the aluminoxane of step (b) with water to form alumina;
   (d) contacting the imine of step (b) with water to form the carbonyl compound and the primary amine.

10. The method of claim 9 further comprising:
    (e) recycling at least a portion of the carbonyl compound of step (d) to step (b).

11. The method of claim 9 further comprising:
    (e) recycling at least a portion of the primary amine or ammonia of step (d) to step (a).

12. The method of claim 11 further comprising:

(f) recycling at least a portion of the carbonyl compound of step (d) to step (b).

13. The method of claim 9 further comprising:

(e) recycling at least a portion of the carbonyl compound and amine of step (d) to step (b).

14. The method of claim 9 further comprising:

(e) recycling at least a portion of the carbonyl compound and amine of step (d) to step (a).

15. A method for the continuous preparation of alumina comprising:

(a) contacting an organoaluminum compound with a first portion of a primary amine to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;

(b) contacting a first portion of a carbonyl compound comprising an aldehyde or ketone with the organoaluminum derivative of step (a) to form a first portion of imine and aluminoxane;

(c) contacting the aluminoxane of step (b) with a second portion of the primary amine and a second portion of the carbonyl compound to form a second portion of imine and alumina;

(d) contacting the imine of steps (b) and (c) with water to form the carbonyl compound and the primary amine.

16. A method for the preparation of an alumina precursor comprising:

(a) contacting a first portion of an organoaluminum compound with a primary amine to form a first portion of an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;

(b) contacting a carbonyl compound comprising an aldehyde or ketone and a chelating imine with a second portion of the organoaluminum derivative of step (a) to form a first aluminoxane adduct;

(c) contacting the first aluminoxane adduct chelate of step (b) with a second portion of the organoaluminum compound of step (a) to form a second aluminoxane adduct; and (d) contacting the second aluminoxane adduct of step (c) with water to form an imine and alumina precursor.

17. The method of claim 16 further comprising:

(f) adding at least a portion of the second adduct of aluminoxane and imine of step (d) to step (a) to form a new composition.

18. The method of claim 17 further comprising:

(f) contacting the new composition of step (e) with water to form alumina and imine.

19. A method for preparing alumina having a bimodal pore size distribution comprising:

(a) contacting an organoaluminum compound with a primary amine to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;

(b) contacting a first carbonyl compound comprising an aldehyde or ketone with a first portion of the organoaluminum derivative to produce a first portion of imine and a first portion of aluminoxane;

(c) contacting the first portion of aluminoxane with water to produce alumina with an average pore size distribution of $D_1$;

(d) contacting a second carbonyl compound comprising an aldehyde or ketone with a second portion of the organoaluminum derivative to produce a second portion of imine and a second portion of aluminoxane;

(e) contacting the second portion of aluminoxane with water to produce alumina with an average pore size distribution of $D_2$.

20. A method for preparing mixtures of alumina and aluminoxanes comprising:

(a) contacting an organoaluminum compound with a primary amine to form an organoaluminum derivative comprising an organoaluminum amide or imide, wherein the organoaluminum compound comprises at least one selected from the group consisting of $R_3Al$, $R_2AlX$, and $RAlX_2$, where each R is independently an alkyl, X is selected from the group consisting of hydrogen, halogens and alkenes;

(b) contacting a first portion of a carbonyl compound comprising an aldehyde or ketone with a first portion of the organoaluminum derivative of step (a) to form a first portion of aluminoxane and a first portion of imine;

(c) contacting the first portion of aluminoxane of step (b) with water to form alumina;

(d) contacting the second portion of organoaluminum derivative of step (a) with a second portion of the carbonyl compound to form a second portion of aluminoxane and a second portion of imine; and (e) combining the second portion of aluminoxane of step (d) with the alumina of step (c).

* * * * *